United States Patent
Brass et al.

(10) Patent No.: US 6,849,254 B1
(45) Date of Patent: Feb. 1, 2005

(54) HCV COMBINATION THERAPY

(75) Inventors: Clifford A. Brass, Scotch Plains, NJ (US); Paul W. Glue, Flemington, NJ (US); Edward Piken, Palos Verdes Estates, CA (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/551,341

(22) Filed: Apr. 18, 2000

Related U.S. Application Data

(60) Provisional application No. 60/129,991, filed on Apr. 19, 1999.

(51) Int. Cl.[7] .................. A61K 38/21; A61K 31/70; A61K 31/355; A61K 31/34
(52) U.S. Cl. .................. 424/85.7; 424/85.4; 514/42; 514/458; 514/474
(58) Field of Search .................. 514/42, 458, 474; 424/85.4, 85.7, 88.7

(56) References Cited

U.S. PATENT DOCUMENTS

| | | | | |
|---|---|---|---|---|
| 4,917,888 | A | * 4/1990 | Katre et al. | 424/85.91 |
| 5,951,974 | A | 9/1999 | Gilbert et al. | 424/85.7 |
| 6,172,046 | B1 | 1/2001 | Albrecht | 514/43 |
| 6,472,373 | B1 | 10/2002 | Albrecht | 514/43 |

FOREIGN PATENT DOCUMENTS

| WO | WO 98/19670 | 5/1998 |
|---|---|---|

OTHER PUBLICATIONS

Sies et al. Am. J. Clin Nutr., 1995, vol. 62, pp. 1315S–1321S.*
www.bayercare.com, One–A–Day 50 Plus and One–A–Day Antioxidant product sheets.*
Abella et al. Brit. J. Clin. Pharmacol., 1996, vol. 42, pp. 731–747.*
Brass, C.A., et al., "Do Antioxidants Ameliorate Ribavirin Related Anemia in HCV Patients", Gastroenterology, (Apr., 1999) vol. 116, No. 4, Part 2, pp. A1192–A1193 (Mail date Mar. 24, 1999).
G.L. Davis, et al., N. Eng. J. Med., 1998, 339:1493–1499.
John G. McHutchinson, et al, N. Eng. J. Med., 1998, 339: 1485–1492.
T. Poynard, et al. , The Lancet, 1998, vol. 352, Oct. 31, pp. 1426–1432.
Reichard, et al., The Lancet, 1998; 351'83–87.
Shulman, Clinical Assessment of Hematologic Effects of Ribavirin in Humans, 1984, pp 79–92.

* cited by examiner

*Primary Examiner*—Janet L. Andres
(74) *Attorney, Agent, or Firm*—Thomas D. Hoffman; Sandy Zaradic

(57) ABSTRACT

Methods of treating patients having susceptible viral infections, especially chronic hepatitis C infection by administering to said patient a therapeutically effective amount of a combination therapy of interferon-alfa and ribavirin for a time sufficient to lower HCV-RNA in association with a therapeutically effective amount of an antioxidant for a time sufficient to ameliorate ribavirin-related hemolysis are disclosed.

20 Claims, No Drawings

HCV COMBINATION THERAPY

This application claims benefit of U.S. Provisional Patent Application No. 60/129,991 filed Apr. 19, 1999.

BACKGROUND OF THE INVENTION

The present invention relates to methods of treating patients having susceptible viral infections, especially chronic hepatitis C infections by administering to said patient a therapeutically effective amount of a combination therapy of interferon-alfa and ribavirin for a time sufficient to lower HCV-RNA in association with a therapeutically effective amount of an antioxidant for a time sufficient to ameliorate ribavirin-related hemolysis.

A chronic hepatitis C viral infection is a particularly insidious and slow-progressing viral disease having a significant impact on the quality of life. It can eventually result in cirrhosis of the liver, decompensated liver disease and/or hepatocellular carcinoma.

Combination treatment with interferon alfa-2b and ribavirin for chronic hepatitis C in patients, is disclosed by Reichard et al.(The Lancet 1998; 351;83–87. T. Poynard et al.(The Lancet, 1998, Vol. 352, October 31, p 1426–1432) disclose that treating chronic hepatitis C patients who had not been treated with interferon or ribavirin with 3 MIU of interferon alfa-2b TIW plus 1000–1200 mg of ribavirin per day for 48 weeks resulted in a sustained virological response at 24 weeks after treatment in 43% of the patients. See also J. G. McHutchinson et al. (N. Engl. J. Med., 1998, 339:1485–1492), G. L. Davis et al. (N. Engl. J. Med., 1998, 339:1493–1499) disclose that treating chronic hepatitis C patients who relapsed after treatment with interferon with 3 MIU of interferon alfa-2b TIW plus 100–1200 mg of ribavirin per day for 48 weeks results in higher rates of sustained virologic response than treatment with interferon alone.

However this combination therapy is not always effective due to side effects associated with ribavirin such as ribavirin-related hemolysis as measured by reduced hemoglobin concentrations. Both McHutchinson, et al and Poynard, et al report that the majority of patients who completed the combination therapy had reached their lowest hemoglobin concentration by the fourth week of combination therapy at which time the hemoglobin concentrations either stabilized or increased. Ribavirin dose reduction to 600 mg/day was reported by McHutchinson, et al for patients with hemoglobin concentrations below 10 g per deciliter and treatment with ribavirin was discontinued in patients with hemoglobin concentration below 8.5 g per deciliter.

There is a need to provide an improved combination therapy for treating susceptible viral infections, especially chronic hepatitis C patients, to ameliorate the ribavirin-related hemolysis throughout the duration of the combination especially in the first 4 to 12 weeks, of therapy so as to produce a sustained virological response in more patients than previously possible.

SUMMARY OF THE INVENTION

The present invention provides methods for treating susceptible viral infections, especially hepatitis C viral infections, which comprises administering to said patient a therapeutically effective amount of ribavirin for a time sufficient to lower viral-RNA in association with a therapeutically effective amount of an antioxidant for a time sufficient to ameliorate ribavirin-related hemolysis.

The present invention provides a method of treating a patient having chronic HCV infection which comprises administering to said patient a therapeutically effective amount of a combination therapy of interferon-alfa and ribavirin for a time sufficient to lower HCV-RNA in association with a therapeutically effective amount of an antioxidant for a time sufficient to ameliorate ribavirin-related hemolysis.

The present invention provides a method of treating a patient having a chronic HCV infection which comprises administering to said patient for a first time period of at least about 24 weeks a therapeutically effective amount of a combination therapy of interferon alfa and ribavirin sufficient to lower detectable HCV-RNA in association with a therapeutically effective amount of an antioxidant sufficient to ameliorate ribavirin-related hemolysis. In a preferred embodiment, the therapeutically effective amount of the combination therapy of interferon alfa and ribavirin is administered in a first time period of about 24 weeks for patients with HCV genotype 2 or 3, or in a first time period of about 48 weeks for patients with HCV genotype 1.

The present invention also provides a method of treating a patient having a chronic HCV infection which comprises (a) administering to said patient for a first time period a therapeutically effective amount of a combination therapy of interferon alfa and ribavirin sufficient to lower detectable HCV-RNA in association with a therapeutically effective amount of an antioxidant sufficient to ameliorate ribavirin-related hemolysis and (b) thereafter administering about 600 to about 1600 mg/day of ribavirin in association with the antioxidant for a second time period of at least about 24 weeks after the end of the first time period. In another preferred embodiment, the therapeutically effective amount of a combination therapy of interferon alfa and ribavirin is administered in a first time period of at least about 24 weeks, more preferably at least about 48 weeks.

The preferred interferon-alfa is interferon-alfa-2a or interferon-alfa-2b; use of interferon-alfa-2b is more preferred.

In a preferred embodiment, the present invention relates to a method of treating patients having chronic hepatitis C infection to eradicate detectable HCV-RNA comprising (a) administering to said patient, in a first treatment time period of twenty-four weeks, a therapeutically effective amount of an antioxidant sufficient to ameliorate ribavirin-related hemolysis in association with a combination of about 800 to 1200 mg per day of ribavirin and a therapeutically effective amount of interferon-alfa-2b in accordance with the following regimin: about 10 MIU daily of interferon-alfa-2b for two weeks, followed by 5 MIU daily of interferon-alfa for six weeks, followed by 3 MIU daily of interferon-alfa interferon-alfa for sixteen weeks, followed by (c) admdinistering in a second treatment time period of twenty-four weeks about 800 to 1200 mg per day of ribavirin and 3 MIU TIW of interferon-alfa in association, a therapeutically effective amount of an antioxidant sufficient to ameliorate ribavirin-related hemolysis.

The preferred antioxidants are Vitamin E derivatives including, but not limited to, d-alpha-tocopheerol and esters thereof, for example, the water soluble d-alpha-tocopheryl polyethylene glycol esters such as the water dispersible Vitamin E d-alpha-tocopheryl polyethylene glycol 1000 succinate("Vitamin E-TPGS") as well as use of compositions of Vitamin E-TPGS and at least one fatty acid ester of glycerine having an overall melting point of 40° C. (both of which are disclosed in U.S. Pat. No. 5,234,695 and available from Eastman Kodak Co., Rochester, N.Y.).

DETAILED DESCRIPTION

The present invention provides methods for treating susceptible viral infections, especially hepatitis C viral infections.

The term "susceptible viral infections" as used herein means viral infections caused by a wide range of RNA and DNA viruses, including, but not limited to, the families of viruses such as flaviruses-including the genus flavirus, pestivirus of which Kunjin virus is a member, and hepavirus of which hepatitis C virus is a member, and arbovirus of which the West Nile virus is a member-orthomyxoviruses, paramyxoviruses, arenaviruses, bunyaviruses, herpes viruses, adenoviruses, poxviruses, and retroviruses.

Typical suitable "susceptible viral infections" include influenza A and B viral infections; parainfluenza viral infections, respiratory syncytial virus("RSV") infections such as RSV bronchiolitis and RSV pneumonia especially such RSV infections in children and infants as well as RSV pneumonia in patients with preexisting cardiopulmonary disease, measles viral infections, Lassa fever viral infections, Korean Haemorrhagic fever infections, hepatitis B viral (HBV) infections, Crimean Congo-Haemorrhagic and HCV infections and HIV-1 infections, encephalitis infections such as caused by West Nile virus or Kunjin virus or the St. Louis encephalitis infections as well as viral infections found in immunocompromised patients. Other susceptible viral infections are disclosed in U.S. Pat. No. 4,211,771 at column 2, line 21 to column 3 line 37; doses and dose regimens and formulations are disclosed at column 3, line 4 to column 9, line 5; see also Canadian Patent No. 1,261,265. Sidwell, R. W., et al. Pharmacol. Ther., 1979, Vol 6 pp 123–146 discloses that the in vivo antiviral experiments conducted with ribavirin generally confirm one broad-spectrum antiviral activity seen in vitro and states that the efficacy of ribavirin is quite dependent upon the site of infection; the manner of treatment; the age of the animal and the virus dosage utilized. Tables 4 and 5 on page 127 list the RNA and DNA virus infections significantly inhibited in vivo by ribavirin.

In a preferred embodiment, the present invention provides an improved method of treating patients having hepatitis C infection by allowing such patients to continue using the therapeutically effective amount of combination therapy of interferon alfa-2b and ribavirin such as approved by the FDA as well as other interferon alfa and ribavirin therapies under clinical development, e.g., pegylated interferon alfa 2a or 2b and ribavirin or described hereinafter. In a pilot study, twelve treatment-naive patients having chronic hepatitis C who received over the counter preparations of the antioxidants vitamin C (1000 mg/day) and vitamin E (800 International Units/day) in combination with the FDA-approved combination therapy of 1000/1200 mg of ribavirin in two divided doses daily (1000 mg if body weight<75 kg) and interferon alf-2b, 3 million International Units ("MIV") subcutaneously ("SC") three times a week ("TIW") were able to continue for four months of the study without having to reduce the ribavirin dose. A control group of fourteen matched relapse patients having chronic hepatitis C received 1000 mg of ribavirin in two divided doses daily and interferon alfa-2b, 3 MIU SC TIW. Hemoglobin levels("HgB") were measured before treatment and at the end of weeks 2, 4, 8 and 12. Baseline HgB values of 14.5–$^+$1.7 and 15.2–$^+$1.2 in grams per deciliter("g/dl") were measured for the treatment-naive and relapse patients, respectively. Hemoglobin drops of 0.9, 1.7, 2.3 and 2.7 g/dl were measured in the treatment-naive patients at the end of weeks 2, 4, 8 and 12, respectively. Hemoglobin drops of 2.0, 3.0, 3.0 and 3.1 g/dl were measured in the relapse patients(control). The use of antioxidants in association with the combination therapy in accordance with the present invention markedly lowered the severity of the ribavirin-related hemolytic anemia in the first twelve weeks of the combination therapy compared to historical controls and the relapse patients in the same pilot study. It was noteworthy that no patients receiving the antioxidants needed to reduce the ribavirin dose. However, three of the control patients required ribavirin dose reduction.

The patients treated in accordance with the preferred embodiments should have no detectable HCV-RNA at the end of said 48 week treatment period, also should have no detectable HCV-RNA for at least 24 weeks after the end of said 48 week period.

The present method of treating patients having chronic hepatitis C infections allows delivery of therapeutically effective amount of the combination of ribavirin and of interferon-alfa sufficient to substantially lower detectable HCV-RNA serum levels, preferably by at least two powers of ten, i.e., at least $10^2$ lower than the initial HCV-RNA serum level, and more preferably eradicate detectable HCV-RNA serum levels. i.e., lower them to less than 100 copies/mL while simultaneously ameliorating the ribavirin-related hemolysis.

The term "antioxidant" as used herein means a substance that delays or inhibits hemolysis related to or promoted by administration of ribavirin.

The term "a therapeutically effective amount of an antioxidant" as used herein means an amount of antioxidant in the range of about one to about two hundred and fifty times, preferably about one to about two hundred times, more preferably ten to about one hundred times, most preferably ten to about fifty times the recommended daily dietary allowance ("RDA") of antioxidants (or the recommended daily amount if no RDA is reported for an antioxidant) useful in the methods of the present invention. The antioxidants useful in the methods of the present invention will normally be administered as long as the ribavirin is administered as part of the combination therapy, induction dosing and ribavirin monotherapy delivered to the patient having susceptible viral infections, especially hepatitis C infections.

The term "in association with" as used herein in reference to administration of ribavirin monotherapy or the combination therapy of interferon-alfa and ribavirin with an antioxidant means that the antioxidant is administered prior to, concurrently with, or after administration of the combination therapy. The antioxidant may be administered orally, parenterally (e.g. IM, IP, SC or IV) or topically, e.g. by suppository. Oral ("PO") or parenteral (e.g. subcutaneous) administration is preferred. Oral administration is more preferred. Typically, the antioxidant is administered in single or divided doses concurrently with the ribavirin which may be administered in single or divided doses BID.

Typically, suitable antioxidants include Vitamin A, Vitamin E, Vitamin C, silybum marianum, co-enzyme-Q10, BHA, BHT, N-acetylcysteine, selenium, panavir, lycopene, or mixtures thereof.

Vitamin A is described in Merck Index 11th Edition #9918 (and 4919) at pages 1576–77. The RDA is in the range of about 250 International Units ("IU")/day up to about 2500 IU/day; preferably about 2500 IU/day for newborns and infants.

The term "Vitamin E" as used herein includes all forms of tocopherol including, but not limited to, the naturally occurring and synthetic homologues of the four types of tocopherols (alpha-, beta-, gamma- and delta-tocopherol) and four types of tocotrienols, including esters thereof, e.g., alpha tocopheryl acetate or alpha tocopheryl succinate as well as the dextrorotatoary ("d"), levorotatoary ("l") optical isomers or mixtures of the d and l isomers. The d optical isomers are more active than l isomers and use of the optical isomers of vitamin E is preferred. The effective amount of Vitamin E useful in the present invention is in the range of one to two hundred and fifty (250) times, preferably one to one hundred times the recommended daily dietary allowance ("RDDA") of 3 to 10 alpha tocopherol equivalents per day; i.e., 3–10 mg of d-alpha tocopherol per day. The activity of 1 mg of d-alpha tocopherol is equal to 1 alpha tocopherol equivalents. Since 1 mg of d-alpha tocopherol is equivalent to 1.49 International units (IU) of Vitamin E, about 4.5 to about 15 IU of Vitamin E is the RDDA. The activity of the following Vitamin E derivatives has been measured: one IU of Vitamin E is equivalent to 1 mg of di-alpha tocopheryl acetate, 1 mg of d-alpha tocopheryl acetate has the potency of 1.36 IU of Vitamin E, 1 mg of d-alpha tocopherol has the potency of 1.49 IU of Vitamin E; and 1 mg of d-alpha tocopheryl succinate has the potency of 1.21 IU of Vitamin E; See Goodman & Gilman's *The Pharmacological Basis of Therapeutics*, Ninth Edition, 1996, McGraw-Hill, pages 1549 and 1585–1590.

Suitable Vitamin E derivatves include d-alpha-tocopherol (available from Roche, Nutley, N. J. with a recommended daily allowance, of 10–30 mg per day equal to 200 IU of Vitamin E per day for adults), Vitamin E esters such as Vitamin E acetate and succinate (alpha-tocopheryl acetate and alpha-tocopheryl succinate) as well as water soluble Vitamin E derivatives. Use of water soluble Vitamin E derivatives is preferred.

Water soluble Vitamin E derivatives include pharmaceutically acceptable Vitamin E salts such as Vitamin E phosphate, as well as water soluble tocopheryl polyethylene glycol esters such as those disclosed in U.S. Pat. Nos. 2,680,749, 3,914,430 and 5,234,695; water soluble tocopheryl polyethylene glycol esters are preferred.

Use of d-alpha-tocopheryl polyethylene glycol esters such as the water dispersible Vitamin E d-alpha-tocopheryl polyethylene glycol 1000 succinate("Vitamin E-TPGS") as well as use of compositions of Vitamin E-TPGS and at least one fatty acid ester of glycerine having an overall melting point of 40° C. (both of which are disclosed in U.S. Pat. No. 5,234,695 and available from Eastman Kodak Co., Rochester, N.Y.) are more preferred.

The effective amounts of Vitamin E derivatives, e.g., water soluble Vitamin E derivatives such as Vitamin E-TPGS is in the range of about 200 IU to 20000 IU of Vitamin E /day, preferably about 1000 IU to about 5000 IU of Vitamin E/day, more preferably about 1200 IU to about 2200 IU of Vitamin E/day, in single or divided doses. Dimitrov, N V, et al., Am J Clin Nutr(USA) September 1996, Vol. 64, (3) pages 329–335 reports that administration of 400 IU (269 mg), 800 IU (537 mg) and 1200 IU (807 mg) of Vitamin E-TPGS to healthy volunteers as a single oral dose resulted slight elevation of plasma alpha tocopherol concentrations. Sokool, R J, et al. Gastroenterology,(USA), June 1993, Vol. 104(6) pages 1727–1735 report that a dose of 20–25 IU/kg/day of Vitamin E-TPGS appears to be safe and effective for treating chronic childhood cholestasis. The RDA of Vitamin E-TPGS for pediatrics is in the range of 15–25 IU/kg/day.

Vitamin C (L-ascorbic acid and D-ascorbic acid)is readily available as an over the counter product. See also Merck Index, 11th Edition #855 pp. 130–131. The RDA for Vitamin C is in the range of about 100 to about 200 mg/day, but the use of doses of up to 25 g/day or even 40 g/day have been reported.

Silybum marianum (silymarin), the active ingredient in milk thistle, is available from Magdaus AG, Germany under the LEGALON trade name. The RDA for silymarin is 140 mg/day, capsule, PO.

Coenzyme-Q10 is a vitamin-like substance made by the human body and is also found in organ meats. The RDA for coenzyme-Q10 is about 300 to 400 mg/day.

BHA (butylated hydroxyanisole) (Merck Index, 11th Edition, No. 1547) and BHT (butylated hydroxytolune (Merck Index, 11th Edition, No. 1548 p. 238) are available from Aldrich Chemical Company Inc., Milwaukee, Wis. 53233.

Acetyl cysteine (N-Acetyl-L-cysteine, "NAC") is found in the body. See also Merck Index, 11th Edition, No. 82 p. 14. The RDA for NAC is in the range of about 300 mg/day to 600 mg/day.

Selenium is available from Aldrich Chemical Company Inc., Milwaukee, Wis. 53233. The RDA for selenium is 200 to 600 micrograms/day.

Panavia (4,4'-isopropylidenedithiobis-2,6-di-t-butylphenol) is available from VyrexCorporation, LaJolla, Calif. 92037 (USA). The RDA for Panavia 200 mg to 800 mg/day PO for HIV patients; higher doses stablized or slightly stabilized CD4 levele in Phase I/II clinical trials. See PharmaProjects, section J5A Lycopene is found in tomatoes; see NY TIMES, Apr. 13, 1999, Science Times Section page F 12. The RDA for lycopene is in the range of 5 to 15 mg/day.

The preferred antioxidants are water soluble d-alpha-tocopheryl polyethylene glycol esters such as the water dispersible Vitamin E d-alpha-tocopheryl polyethylene glycol 1000 succinate("Vitamin E-TPGS") as well as use of compositions of Vitamin E-TPGS and at least one fatty acid ester of glycerine having an overall melting point of 40° C. (both of which are disclosed in U.S. Pat. No. 5,234,695 and available from Eastman Kodak Co., Rochester, N.Y.).

Pharmaceutical compositions of the antioxidants suitable for oral, parenteral and topical administration and useful in the present invention may contain the excipient, and other ingredient found in the over the counter preparations of the antioxidants. Compositions of Vitamin E-TPGS and at least one fatty acid ester of glycerine having an overall melting point of 40° C. disposed in U.S. Pat. No. 5,234,695 may also be used. See also the compositions of Trolux and Trolux C disclosed in *J Pharm Pharmacol*(GB), February 1995, Vol 47(2), pages 138–142.

The in vitro inhibitory concentrations of ribavirin are disclosed in Goodman & Gilman's *"The Pharmacological Basis of Therapeutics"*, Ninth Edition, (1996) McGraw Hill, N.Y., at pages 1214–1215. The Virazole product information discloses a dose of 20 mg/mL of Virazole aerosol for 18 hours exposure in the 1999 Physicians Desk Reference at pages 1382–1384.

Ribavirin dosage and dosage regimens are also disclosed by Sidwell, R. W., et al. Pharmacol. Ther 1979 Vol 6. pp123–146 in section 2.2 pp 126–130. Fernandes, H., et al., Eur. J. Epidemiol., 1986, Vol 2(1) pp1–14 at pages 4–9 disclose dosage and dosage regimens for oral, parenteral and aerosol administration of ribavirin in various preclinical and clinical studies.

The term "patients having hepatitis C infections" as used herein means any patient-including a pediatric patient-having hepatitis C and includes treatment-naive patients having hepatitis C infections and treatment-experienced patients having hepatitis C infections as well as those pediatric, treatment-naive and treatment-experienced patients having chronic hepatitis C infections.

These patients having chronic hepatitis C include those who are infected with multiple HCV genotypes including type 1 as well as those infected with, inter alia, HCV genotype 2 and/or 3.

The term "pediatric patient" as used herein means a patient below the age of 17, and normally includes those from birth to 16 years of age.

The term "treatment-naive patients having hepatitis C infections" as used herein means patients with hepatitis C who have never been treated with ribavirin or any interferon, including but not limited to interferon-alfa, or pegylated interferon alfa.

The term "treatment-experienced patients having hepatitis C infections" as used herein means patients with hepatitis C who have been treated with ribavirin or any interferon, including but not limited to interferon-alfa, or pegylated interferon alfa, including relapsers and non-responder.

The term "patients having chronic hepatitis C infections" as used herein means any patient having chronic hepatitis C and includes "treatment-naive patients and treatment-experienced patients having chronic hepatitis C infections, including but not limited to relapsers and non-responders.

The term "relapsers" as used herein means treatment-experienced patients with hepatitis C who have relapsed after initial response to previous treatment with interferon alone, or in combination with ribavirin.

The term "non-responders" as used herein means treatment-experienced patients with hepatitis C who have not responded to prior treatment with any interferon alone, or in combination with ribavirin.

The term "interferon-alfa" as used herein means the family of highly homologous species-specific proteins that inhibit viral replication and cellular proliferation and modulate immune response. Typical suitable interferon-alfas include, but are not limited to, recombinant interferon alfa-2b such as INTRON A interferon available from Schering Corporation, Kenilworth, N.J., recombinant interferon alfa-2a such as ROFERON® interferon available from Hoffmann-La Roche, Nutley, N.J., recombinant interferon alpha-2c such as Berofor alpha 2 interferon available from Boehringer Ingelheim Pharmaceutical, Inc., Ridgefield, Conn. interferon alpha-n1, a purified blend of natural alfa interferons such as SUMIFERON® available from Sumitomo, Japan or as WELLFERON® interferon alpha-n1 (INS) available from the Glaxo-Wellcome Ltd., London, Great Britain, or a consensus alpha interferon such as those described in U.S. Pat. Nos. 4,897,471 and 4,695,623 (especially Examples 7, 8 or 9 thereof) and the specific product available from Amgen, Inc., Newbury Park, Calif., or interferon alfa-n3 a mixture of natural alfa interferons made by Interferon Sciences and available from the Purdue Frederick Co., Norwalk, Conn., under the ALFERON® Tradename or recombinant interferon alpha available from Frauenhoffer Institute, Germany or that is available from Green Cross, South Korea. The use of interferon alfa-2a or alpha 2b is preferred. Since interferon alpha 2b, among all interferons, has the broadest approval throughout the world for treating chronic hepatitis C infection, it is most preferred. The manufacture of interferon alpha 2b is described in U.S. Pat. No. 4,530,901.

The term "pegylated interferon alfa" as used herein means polyethylene glycol modified conjugates of interferon alfa, preferably interferon alfa-2a and -2b. The preferred polyethylene-glycol-interferon alfa-2b conjugate is $PEG_{12000}$-interferon alfa 2b. The phrases "12,000 molecular weight polyethylene glycol conjugated interferon alpha" and "$PEG_{12000}$-IFN alfa" as used herein mean conjugates such as are prepared according to the methods of International Application No. WO 95/13090 and containing urethane linkages between the interferon alfa-2a or -2b amino groups and polyethylene glycol having an average molecular weight of 12000.

The preferred $PEG_{12000}$-interferon alfa-2b is prepared by attaching a PEG polymer to the epsilon amino group of a lysine residue in the IFN alfa-2b molecule. A single $PEG_{12000}$ molecule is conjugated to free amino groups on an IFN alfa-2b molecule via a urethane linkage. This conjugate is characterized by the molecular weight of $PEG_{12000}$ attached. The $PEG_{12000}$-IFN alfa-2b conjugate is formulated as a lyophilized powder for injection. The objective of conjugation of IFN alfa with PEG is to improve the delivery of the protein by significantly prolonging its plasma half-life, and thereby provide protracted activity of IFN alfa.

Other interferon alfa conjugates can be prepared by coupling an interferon alfa to a water-soluble polymer. A non-limiting list of such polymers include other polyalkylene oxide homopolymers such as polypropylene glycols, polyoxyethylenated polyols, copolymers thereof and block copolymers thereof. As an alternative to polyalkylene oxide-based polymers, effectively non-antigenic materials such as dextran, polyvinylpyrrolidones, polyacrylamides, polyvinyl alcohols, carbohydrate-based polymers and the like can be used. Such interferon alfa-polymer conjugates are described in U.S. Pat. Nos. 4,766,106, 4,917,888, European Patent Application No. 0 236 987, European Patent Application Nos. 0510 356, 0 593 868 and 0 809 996 (pegylated interferon alfa-2a) and International Publication No. WO 95/13090.

Pharmaceutical compositions of pegylated interferon alfa-suitable for parenteral administration may be formulated with a suitable buffer, e.g., Tris-HCl, acetate or phosphate such as dibasic sodium phosphate/monobasic sodium phosphate buffer, and pharmaceutically acceptable excipients (e.g., sucrose), carriers (e.g. human plasma albumin), toxicity agents (e.g. NaCl), preservatives (e.g. thimerosol, cresol or beraylalcohol), and surfactants(e.g. tween or polysorabates) in sterile water for injection. The pegylated interferon alfa—may be stored as lyophilized powders under a refrigeration at 2°–8° C. The reconstituted aqueous solutions are stable when stored between 2° and 8° C. and used within 24 hours of reconstitution. See for example U.S. Pat. Nos. 4,492,537; 5,762,923 and 5,766,582. The reconstituted aqueous solutions may also be stored in prefilled, multi-dose syringes such as those useful for delivery of drugs such as insulin. Typical suitable syringes include systems comprising a prefilled vial attached to a pen-type syringe such as the NOVOLET Novo Pen available from Novo Nordisk, as well as prefilled, pen-type syringes which allow easy self-injection by the user. Other syringe systems include a pen-type syringe comprising a glass cartridge containing a diluent and lyophilized pegylated interferon alfa powder in a separate compartment.

The following preferred embodiments for administering therapeutically effective amounts of the combination therapy of interferon alfa and ribavirin are presented The interferon-alpha administered as part of the combination therapy is preferably selected from interferon alpha-2a, interferon alpha-2b, a consensus interferon, a purified interferon alpha product or a pegylated interferon-alpha. More preferably, the interferon-alpha is selected from interferon alpha-2a, interferon alpha-2b, or a purified interferon alpha product and the amount of interferon-alpha administered is from 2 to 10 million IU per week on a weekly, TIW, QOD or daily basis. In a preferred embodiment, the interferon-alpha administered is interferon-alpha-2b and the amount of interferon-alpha is administered 3 million IU TIW.

Alternatively, the interferon-alpha administered as part of the combination therapy is consensus interferon and the amount of interferon-alpha administered is from 1 to 20 micrograms per week on a weekly, BIW, TIW, QOD or daily basis. In another embodiment, the interferon-alpha administered is a pegylated interferon alpha-2b and the amount of interferon-alpha administered is from 0.5 to 2.0 micrograms per week on a weekly, BIW, TIW, QOD or daily basis. Alternatively, the interferon-alpha administered is a pegylated interferon alpha-2a and the amount of interferon-alpha administered is from 20 to 250 micrograms/kilogram per week on a weekly, TIW, QOD or daily basis.

When the pegylated interferon-alfa administered as part of the combination therapy is a pegylated interferon alfa-2b, the therapeutically effective amount of pegylated interferon alfa-2b administered during the treatment in accordance with the present invention, including in first and second treatment time periods, is in the range of about 0.1 to 9.0 micrograms per kilogram of pegylated interferon alfa-2b administered per week, in single or divided doses, preferably once a week (QW) or twice a week(BIW), preferably in the range of about 0.1 to about 9.0 micrograms per kilogram of pegylated interferon alfa-2b administered once a week (QW) or in the range of about 0.05 to about 4.5 micrograms per kilogram of pegylated interferon alfa-2b administered twice a week(BIW), or is in the range of about 0.5 to about 3.0 micrograms per kilogram of pegylated interferon alfa-2b administered per week, preferably in the range of about 0.5 to about 3.0 micrograms per kilogram of pegylated interferon alfa-2b administered once a week (QW) or in the range of about 0.25 to about 1.5 micrograms per kilogram of pegylated interferon alfa-2b administered twice a week, or is in the range of about 0.75 to about 1.5 micrograms per kilogram of pegylated interferon alfa-2b administered per week, most preferably is in the range of about 0.75 to about 1.5 micrograms per kilogram of pegylated interferon alfa-2b administered once a week or about 0.375 to about 0.75 micrograms per kilogram of pegylated interferon alfa-2b administered twice a week.

When the pegylated interferon-alfa administered to pediatric patients as part of the combination therapy is a pegylated interferon alfa-2b, the therapeutically effective amount of pegylated interferon alfa-2b administered during the treatment in accordance with the present invention, including in first and second treatment time periods is in the range of about 0.1 to 9.0 micrograms per kilogram of pegylated interferon alfa-2b administered per week, in single or divided doses, preferably once a week (QW) or twice a week(BIW), more preferably about 0.1 to about 9.0 micrograms per kilogram of pegylated interferon alfa-2b administered once a week (QW), or about 0.05 to about 4.5 micrograms per kilogram of pegylated interferon alfa-2b administered per week, in single or divided doses, preferably once a week (QW) or twice a week(BIW), more preferably about 0.05 to about 4.5 micrograms per kilogram of pegylated interferon alfa-2b administered once a week, or preferably about 0.75 to about 3.0 micrograms per kilogram of pegylated interferon alfa-2b administered in single or divided doses, preferably once a week (QW) or twice a week(BIW), more preferably about 0.75 to about 3.0 micrograms per kilogram of pegylated interferon alfa-2b administered once a week or about 0.375 to about 1.5 micrograms per kilogram of pegylated interferon alfa-2b administered twice a week, and most preferably about 2.25 to about 2.6 micrograms per kilogram of pegylated interferon alfa-2b administered once a week or about 1.1 to about 1.3 micrograms per kilogram of pegylated interferon alfa-2b administered twice a week(BIW).

When the pegylated interferon-alfa administered as part of the combination therapy is a pegylated interferon alfa-2a, the therapeutically effective amount of pegylated interferon alfa-2a administered during the treatment in accordance with the present invention, including in first and second treatment time periods, is in the range of about 50 micrograms to about 500 micrograms once a week("QW"), preferably about 180 micrograms to about 250 micrograms QW or the effective amount is in the range of about 50 micrograms to about 250 micrograms twice a week, preferably about 90 micrograms to about 125 micrograms twice a week.

When the pegylated interferon-alfa administered to a pediatric patient as part of the combination therapy is a pegylated interferon alfa-2a, the therapeutically effective amount of pegylated interferon alfa-2a administered during the treatment in accordance with the present invention, including in first treatment time period is in the range of about 50 micrograms to about 500 micrograms once a week("QW"), preferably about 300 micrograms to about 375 micrograms QW or the therapeutically effective amount of pegylated interferon alfa-2a administered to a pediatric patient is in the range of about 50 micrograms to about 250 micrograms twice a week, preferably about 150 micrograms to about 190 micrograms once a week Ribavirin is administered as part of the combination therapy to the patient in association with pegylated interferon-alfa, that is, before, after or concurrently with the administration of the pegylated interferon alfa. The pegylated interferon-alfa dose is preferably administered during the same period of time that the patient receives doses of ribavirin. The amount of ribavirin administered concurrently with the pegylated interferon-alfa is from about 400 to about 1600 mg per day, preferably about 600 to about 1200 mg/day or about 800 to about 1200 mg day and most preferably about 1000 to about 1200 mg/kg a day. The pegylated interferon-alfa dose is also preferably administered to the pediatric patient during the same period of time that such patient receives doses of ribavirin. The amount of ribavirin administered to the pediatric patient concurrently with the pegylated interferon-alfa is from about 8 to about 15 mg per kilogram per day, preferably about 8, 12 or 15 mg per kilogram per day, in divided doses.

The following preferred embodiments for administering induction dosing amounts of interferon alfa in association with ribavirin in the first and second treatment time periods are presented.

The amount of ribavirin administered in the first treatment time period is from 400 to 1600 mg per day, preferably 600 to 1200 mg/day or about 800 to 1200 mg day and most preferably about 1000 to 1200 mg/kg a day. The amount of ribavirin administered in the second treatment time period is in the range of from about 800 to 1200 mg per day, preferably from about 1000 to 1200 mg per day.

When the interferon-alfa administered is selected from interferon alfa-2a, interferon alfa-2b, or a purified interferon alfa product, the therapeutically effective induction dosing amount of interferon-alfa administered in the first treatment time period is 10 MIU daily for 2 weeks, followed by 5 MIU daily for 6 weeks, followed by 3 MIU daily for 16 weeks, and the therapeutically effective amount of interferon-alfa administered in the second treatment time period is 3 MIU TIW for 24 weeks.

When the interferon-alfa administered is interferon-alfa-2b, the therapeutically effective induction dosing amount of interferon-alfa-2b administered in the first treatment time period is 10 MIU daily for 2 weeks, followed by 5 MIU daily for 6 weeks, followed by 3 MIU daily for 16 weeks, and the amount of interferon-alfa-2b administered in the second treatment time period is 3 MIU TIW for 24 weeks.

When the interferon-alfa administered is consensus interferon, the amount of consensus interferon administered in the first treatment period of twenty-four weeks is from 15 to 20 micrograms on a daily basis for two weeks, followed by 9 to 15 micrograms on a daily basis for twenty-two and the amount of consensus interferon administered in the second treatment period is from 9 micrograms TIW for twenty-four weeks.

In a preferred embodiment of the present invention, the interferon-alfa is interferon-alfa-2a or -2b; use of interferon-alfa-2b is more preferred.

The sum of the first and second treatment time periods is about 40–50 weeks, and preferably is 48 weeks.

A person suffering from chronic hepatitis C infection may exhibit one or more of the following signs or symptoms:

(a) elevated ALT, (b) positive test for anti-HCV antibodies, (c) presence of HCV as demonstrated by a positive test for HCV-RNA, (d) clinical stigmata of chronic liver disease, (e) hepatoceluar damage.

To practice the invention, the combination therapy of interferon-alfa and ribavirin or inducing dosing amounts of interferon-alfa and ribavirin are administered to the patient exhibiting one or more of the above signs or symptoms in amounts sufficient to eliminate or at least alleviate one or more of the signs or symptoms. The therapeutically effective amount of the antioxidant is administered in association with the combination therapy or induction dosing amounts to ameliorate the ribavirin-related hemolysis.

Ribavirin is administered to the patient in association with the interferon-alfa, that is, the interferon-alfa dose is administered during the same period of time that the patient receives doses of the ribavirin derivative of the present invention. Most interferon-alfa formulations are not effective when administered orally, so the preferred method of administering the interferon-alfa is parenterally, preferably by subcutaneous, IV, or IM, injection. Ribavirin may be administered orally in capsule or tablet form in association with the parenteral administration of interferon-alfa. Of course, other types of administration of both medicaments, as they become available are contemplated, such as by nasal spray, transdermally, by suppository, by sustained release dosage form, etc. Any form of administration will work so long as the proper dosages are delivered without destroying the active ingredient.

Pharmaceutical composition of interferon-alfa, suitable for parenteral administration may be formulated with a suitable buffer, e.g., Tris-HCl, acetate or phosphate such as dibasic sodium phosphate/monobasic sodium phosphate buffer, and pharmaceutically acceptable excipients (e.g., sucrose), carriers (e.g. human serum albumin), toxicity agents (e.g. NaCl), preservatives (e.g. thimerosol, cresol or benylalcohol), and surfactants(e.g. tween or polysorabates) in sterile water for injection. The interferon alfa—may be stored as lyophilized powders under a refrigeration at 2°–8° C. The reconstituted aqueous solutions are stable when stored between 2° and 8° C. and used within 24 hours of reconstitution. See for example U.S. Pat. Nos. 4,492,537; 5,762,923 and 5,766,582.

The term "no detectable HCV-RNA" in the context of the present invention means that there is less than 100 copies of HCV-RNA per ml of serum of the patient as measured by quantitative, multi-cycle reverse transcriptase PCR methodology. HCV-RNA is preferably measured in the present invention by the methodology described below. This methodology is referred to herein as HCV-RNA/qPCR.

The term "substantially lower detectable HCV-RNA serum levels" in the context of the present invention means that the HCV-RNA serum level is lower by at least a power of ten, preferably lower by two powers of ten and most preferably lower by at least three powers of ten, compared to the initial HCV-RNA serum level.

RNA is extracted from patient serum using a guaninidium thiocyanate-phenol-chloroform mister followed by ethanol-ammonium acetate precipitation. The precipitated RNA is centrifuged and the resulting pellet is dried in a CEN-TRIVAP™ console (Labconco, Kansas City, Mo.). The dry pellet is then resuspended in 30 microliters of an Rnasin (Promega Corp., Madison, Wis.), dithiothritol, and diethylpyrocarbonate-treated water mixture. Samples are kept at or below −20° C. (preferably below −70° C.) until RNA reverse transcription (RT) and PCR.

In order to convert the entire RNA sequence into cDNA in the RT reaction, random hexadeoxyribonucleotides (Pharmacia Biotech, Piscataway, N.J.) are used as primers for the first strand cDNA synthesis. Two aliquots of 3 microliters of resuspended sample is added to 3 microliters of 100 ng/$\mu$l random primers and denaturated at 70° C., then reverse transcribed at 40° C. for one hour using M-MLV reverse transcriptase (USB, Cleveland, Ohio) in standard buffer containing 5 mM $MgCl_2$. The final RT reaction volume is 26 $\mu$l. The PCR is started immediately following the reverse transcription.

A modified version of the PCR method is performed using heat-stable Taq polymerase to amplify the cDNA. Seventy-five microliters of PCR mix is added to the entire RT reaction volume (26 $\mu$l) to a final $MgCl_2$ concentration of 1.5 mM in a total volume of 101 $\mu$l. Each 101 $\mu$l sample is then split into 50.5 $\mu$l, and a layer of mineral oil is placed on top to prevent evaporation.

The PCR cycle consists of annealing for 90 sec., extension for 90 sec., and denaturation for 90 sec., at 55° C., 74° C. and 94° C., respectively. Thermocycling samples is submitted to a final 74° C. extension for 10 minutes. Four different cycle sets are used. By loading the sample in duplicate, and splitting these samples evenly after RT, there are four tubes from one sample. Each of the four tubes is given a different cycle number, enhancing sensitivity and accuracy in the quantitation process. The thermocycling efficiency will be assessed by satisfactory amplification of known copy number RNA standards included in each set of 60 tubes. Two primer sets are used for the amplification, both from the 5' untranslated region of the HCV genome. Both of these primer sets are highly conserved and detect all known subtypes of HCV. Primer set 1: upstream 5'-GTG GTC TGC GGA ACC GGT GAG T-3', downstream 5'-TGC ACG GTC TAC GAG ACC TC-3' which produced a 190 bp product. Primer set 2: upstream 5'-CTG TGA GGA ACT ACT GTC TTC-3', downstream 5'-CCC TAT CAG GCA GTA CCA CAA-3' which produced a 256 bp product.

The amplified cDNA is then electrophorised in 3% agarose gel and transferred to nylon membrane. The target DNA is detected by Southern blotting and immunostaining using a nonradioactive digoxigenin-labeled DNA probe. These procedures are performed using automated instruments for PCR thermocycling, agarose gel electrophoresis, vacuum-transfer Southern blot, hybridization, and immunostaining. Each membrane contains known copy number serially diluted standards which are used to construct standard curves for quantitative measurement of the specimen bands. Originally standard curves are made from carefully diluted HCV-RNA from transcribed clones. Radioactive incorporation studies, gel electrophoresis, and OD 260 are performed on the transcripts to determine that they are of the expected length. After the production of the RNA transcripts quantitated clone standards "pooled" standards are generated which better represent the heterogeneous nature of HCV, one would encounter in natural infection. These pools are made by combining large amounts of serum or plasma from known infected individuals. The serum/plasma pools are calibrated with PCR, against the clone transcripts and then diluted in the known PCR-negative fluids. Finally, the higher copy number samples of the pools are checked against the cDNA Quantiplex nucleic acid detection system from Chiron Inc. (Emeryville, Calif.). These "double quantitated" pools are aliquoted and saved at −70° C. Dilutions of 5,000,000, 1,000,000, 500,000, 100,000, 10,000, and 1000 copies/ml are used in each experiment.

Each Southern blot membrane is scanned into a computer using an automated scanner/densitometer, at intervals during development to determine when the standard curve is most linear. The resultant electronic images are then measured for band area and mean band density. All of the reading are standardized to integrated band density and compared to the standard curve to obtain a numerical value of viral copy number for each band.

The term "sustained virologic response" as used in the context of the present invention means that there is no detectable HCV-RNA in the patients treated in accordance with the present invention for at least 24 weeks after the end of the combined therapy treatment. Preferably, the period of sustained virologic response will be at least one year—or longer—after the end of treatment.

During treatment and post-treatment follow-up, biochemical (ALT), virological (HCV-RNA), hematology, including at least the following hemoglobin(HgB), hematocrit(HCT). RBC, WBC with differential and platelet counts) levels and histological (liver biopsy) examinations would be used to assess the nature and duration of response to study treatment. The primary efficacy variable will be the overall response defined as loss of serum HCV-RNA/qPCR (<100 copies/mL) as measured at 24 weeks following the end of therapy. In addition, the drop in the hemoglobin levels compared to baseline values will also be measured. In addition, a decrease in hepatic inflammation, an improvement in post-treatment liver biopsy as measured by the Knodell Histology Activity index (HAI) and normalization of ALT will also be examined as a secondary efficacy endpoints. The safety of the study treatments will be assessed by monitoring selected laboratory parameters and by also recording and evaluating the occurrence of any adverse events.

Efficacy

The primary efficacy objective will be the comparison of the treatment groups 1 and 2 with respect to the sustained virologic response rate defined as loss of (detectable) serum HCV-RNA/qPCR measured at 24 weeks following the end of therapy to an undetectable level or to a level <100 copies/mL. The following secondary efficacy Endpoints will also be examined using logistic regression:

The secondary efficacy Endpoints:

proportions of patients with normalization of ALT at 24 weeks of follow-up;

proportions of patients with improvement in biopsy (Categories I+II+III combined scores);

changes from Baseline in the biopsy scores (Categories I+II+III combined scores);

response rates at Endpoint of treatment based on HCV-RNA/qPCR;

proportion of patients with normalization of ALT at Endpoint of treatment.

response rates at 24 weeks of follow-up based on HCV-RNA/qPCR.

Virology: Entry Status and Change from Entry

Serum HCV-RNA/qPCR testing and HCV genotype testing will be performed by a central laboratory. A positive HCV-RNA assay result will be required at Baseline; only patients positive for HCV-RNA will be eligible to participate. Repeat assays should be scheduled at Weeks 4, 12, 24, and if the patient is in the 48 week treatment groups at weeks 36 and 48. All patients should have repeat assays scheduled for Follow-up Weeks 12 and 24.

Response will be assessed as defined below:

| | |
|---|---|
| Virologic Responder: | A patient will be classified as a responder at a given time point if HCV-RNA/qPCR is negative (<100 copies per mL) at that time point. |
| Sustained Virologic Responder: | A patient will be classified as a sustained responder if the patient is a responder at 24 weeks of follow-up. Note that patients who do not meet these criteria including patients who discontinued before the required HCV-RNA/qPCR evaluations are obtained, will be classified as non-responders. |
| Overall Responder: | Based on both serum HCV-RNA/qPCR and change in liver histology as evaluated by the Knodell HAI Inflammation Score. A patient will be classified as an overall responder to treatment if at 24 weeks of follow-up, he/she is a sustained virologic responder and has normal ALT. |

Liver Histology

Liver biopsy will be taken within the six months preceding patient enrollment and at Follow-up Week 24 for all patients. Evaluation of the biopsies will be performed by a single pathologist using the Knodell Histology Activity Score. The central pathologist will be blinded with respect to patient identification, treatment group, and the time the biopsy will be obtained relative to treatment (Pre- or Post-treatment). Efficacy of study treatments will be assessed by comparing the degree of inflammatory activity observed at Baseline with that present at Follow-up Week 24.

The patient's weight and their baseline disease characteristics (HCV genotype, hemoglobin levels and initial viral load) for all patients will be measured before the start of the study. HCV genotypes should be done on the patient serum samples subjected to HCV-RNA/qPCR testing.

This enhancement of efficacy included all aspects of the disease will result in:

Sustained eradication of detectable HCV-RNA;

Improvement in hepatic inflammation;

Lower Hemoglobin Drops;

Normalization of ALT;

Improvement in HQL.

Clinical Study Design

This is a treatment protocol designed to confirm the efficacy of Vitamin E shown in the pilot study discussed herein above in the amelioration of hemolysis associated with REBETRON® (INTRON A®+Ribavirin) for treatment of patients with chronic hepatitis C.

The following double blind treatment arms will be randomly assigned to patients at selected centers sunder this protocol:

REBETRON® (INTRON A® 3 MU TIW_Ribavirin 1000–12000 mg po daily in divided doses) plus 1000 IU of Vitamin E, BID.

B REBETRON® (INTRON A® 3MU TIW+Ribavirin 1000–12000 mg po daily in divided doses) plus 1000 IU of Vitamin E plus placebo.

C. REBETRON® (INTRON A® 3 MU TIW+Ribavirin 1000–12000 mg po daily in divided doses) plus Matched placebo only.

Patients must weigh≧75 kg will receive 1200 mg/day of ribavirin.

Treatment will be discontinued it patients do not clear virus by 6 months.

A total of 90 patients will be enrolled (30 patients per group).

Objectives

The primary objective of this treatment protocol is to confirm that Vitamin E can reduce the hemolysis that occurs with the use of ribavirin, (a reduction in the drop of hemoglobin from baseline compared to control).

The secondary objectives are to determine if there is a decrease need for ribavirin does reductions, a decrease in patient discontinuations from therapy and an improved quality of life.

Study Synopsis

The protocol is a double blind randomized study of standard dose REBETRON (INTRON A® 3 mu TIW+ Ribavirin 1000–12000 mg/d) plus 1000 IU of Vitamin E or 2000 IU of Vitamin E or Placebo. Serial hemoglobin levels, HCV RNA levels and ribavirn levels will be drawn. Other markers of hemolysis and a quality of life tool (vitality and depression scales) will be used to also measure outcomes. Interim analysis will be done off site at weeks 12 and 24 while investigator sites remain blinded.

Study Population

Adult male and female patients with compensated, chronic hepatitis C who have not recieved previous treatment with interferon. Patients meeting the following Inclusion Criteria will be enrolled.

Inclusion Criteria

The patient must meet the following criteria for entry:

Adult male or female, age of 18 to 70.

Serum positive for hepatitis C virus by PCR.

Liver biopsy prior to entry to this protocol with a pathology report confirming that the historical diagnosis is consistent with chronic hepatitis.

Compensated liver disease with the following laboratory parameters at the Entry visit:

Hemoglobin values of >11 g/dL for females or >12 g/dL for males

WBC>3,000/mm$^3$

Neutrophil count 1,500/mm$^3$

Platelets>70,000mm$^3$

Prothrombin time <2 seconds prolonged compared to control, or equivalent INR ratio Bilirubin within 20% of the upper limit of normal.

Albumin>3.5 g/dL.

Serum creainine<1.4 mg/dL

Fasting blood sugar<115 mg/dL for non-diabetic patients

Hemoglobin A<8.5% for diabetic patients (whether on medication and/or diet controlled).

Thyroid Stimulating Hormone (TSH) within normal limits

Antinuclear antibodies (ANA)<1.160.

Alpha fetoprotein (AFP) value within normal limits obtained within the prior year. For patients with results above the upper limit of normal but <50 ng/mL both of the following are required:

Alpha fetoprotein value<ng/mL obtained within 3 months prior to entry and Ultrasound obtained within 3 months prior to entry that is negative for evidence of hepatocellular carcinoma.

Exclusion Criteria

The patient will be excluded from entry if any of the following criteria apply:

Hypersensitivity to alpha interferon or ribivirin.

Any other causes for chronic liver disease other than chronic hepatitis C.

Hemoglobinopathies (e.g., Thalassemia) or any other cause of hemolytic anemia.

Evidence of advanced liver disease such as a history of or presence of ascites, bleeding varices, or spontaneous encephalophy.

Any known preexisting medical condition that could interfer with the patients participation in the protocol including: CNS trauma or active seizure disorders requiring medication; poorly controlled diabetes mellitus; serious pulmonary disease; immunologically-medicated diseases; gout; or any medical condition requiring, or likely to require during the course of the study, chronic systemic administration of steroids.

Patients with evidence of ischemia on stress testing (required for patients at risk of or with a history of coronary artery disease; EGG evidence of ischemia, an arrhythmia, cardiac failure, coronary surgery, uncontrolled hypertension, angina or a myocardial infarction within 12 months.

Patients with clinically significant retinal abnormalities.

Substance abuses, such as alcohol (80 g/day) I.V. drugs and inhaled drugs. If the patient has a history of substance abuse, to be considered for inclusion into the protocol, the patient must have abstained from using the abused substance for at least 1 year. Patients receiving a methadone within the past year are also excluded.

Patients must be counseled with regard to the need to abstain from the consumption of alcohol. Patients with an alcohol consumption of >20 g/day are ineligible for the protocol.

Concurrent use of nucleoside analogs, amantadine/rimantadine, and protease inhibitors will be excluded.

Patients with a history of organ transplantation with be excluded.

Pre-existing psychiatric conditions; especially severe depression, or a history of severe psychiatric disorder, such as major psychoses, suicidal ideation and/or suicidal attempt are excluded.

Study Medication

Ribavirin Supplies

Study medication will be provided in the standard packaging of Rebetron. Ribavirin will be provided by the patient's pharmacy, directly from office dispensing or through Schering's Commitment to Care program. Ribavirin capsules must be stored at room temperature of 15–25° C.(59–77° F.).

Administration of Ribavirin

Ribavirin will be administered by the oral route twice daily (BID) at doses ranging from 600 to 1200 mg per day. Ribavirin doses above 800 mg will be based patient weight at the Entry visit as indicated on the following table:

TABLE

| Ribavirin Dose | Patient Weight | Total Daily Dose | Regimen (200 mg each) | Total Number Capsules/Dose |
|---|---|---|---|---|
| | <75 kg | 1000 mg | 400 mg/600 mg divided doses, BID, | 2 capsules am 3 capsules pm |
| | ≧75 kg | 1200 mg | 600 mg/600 mg divided doses, BID | 3 capsules am 3 capsules pm |

All ribavirin doses will be administered on a BID schedule. If an adverse event occurs for which a dose reduction is required, the Total Daily Dose should be adjusted.

Intron A Supplies

Intron A will be obtained by the patient in the appropriate strength in order to provide doses of 3 MU TIW. This will be obtained from the patient's pharmacy, directly from office dispensing, or through Schering Corporation's Commitment to Care program.

Administration of Intron A

Intron A will be administered by the subcutaneous route. Please see the Intron A Package Insert for additional information.

Vitamin E placebo supplies and administration.

Vitamin E (available from R. P. Scherer Corp, St Petersburg, Fla.) will be supplied in capsule form of 500 IU of Vitamin E strength. The capsules will be packaged in a generic bottle. Appropriately matched placebo capsules will also be supplied in generic bottles. These will be supplied directly from Schering-Plough Corporation. Capsules will be packaged in 1 month supplies in accordance with the study group (vitamin E/vitamin E), vitamin E/placebo, or placebo/placebo). Each patients will take two capsules AM and two capsules PM on a daily basis as follows: for the study group (vitamin E/vitamin E)—two 500 IU vitamin E capsules AM and two vitamin E capsules PM.;for the study group (vitamin E/placebo)—two 500 IU vitamin E capsules AM and two placebo capsules PM.; and :for the study group (placebo/placebo)—two placebo capsules AM and two placebo capsules PM.

Duration of Treatment

Duration of treatment with both Intron A and ribavirin will be for up to 48 weeks.

We expect that he use of antioxidants in association with the combination therapy in accordance with the Clinical Study Design of the present invention will markedly lower the severity of the ribavirin-related hemolytic anemia in the first twelve weeks of the combination therapy—and continue to maintain a lowerer ribavirin-related hemolytic anemia level—throughout the duration of the combination therapy—compared to historical controls

---

What is claimed is:

1. A method of treating a patient having chronic HCV infection which comprises administering to said patient a therapeutically effective amount of a combination therapy of interferon-alfa and ribavirin for a time sufficient to substantially lower HCV-RNA in association with a therapeutically effective amount of Vitamin E and Vitamin C for a time sufficient to ameliorate ribavirin-related hemolysis wherein the therapeutically effective amounts of Vitamin E and of Vitamin C are in the range of about ten to about one hundred times the recommended daily dietary allowance of Vitamin E and of Vitamin C.

2. The method of claim 1 wherein the interferon alfa is interferon alfa-2a, interferon-alfa-2b, pegylated interferon alfa-2a, pegylated interferon alfa-2b, or a consensus interferon or a purified interferon alfa product.

3. The method of claim 1 wherein Vitamin E is a water soluble Vitamin E derivative.

4. The method of claim 3 wherein the water soluble Vitamin E derivative is an alpha-tocopheryl polyethylene glycol ester.

5. The method of claim 4 wherein the water soluble Vitamin E derivative is an alpha-tocopheryl polyethylene glycol succinate ester.

6. The method of claim 1 wherein the combination therapy comprising 3 Million International Units ("MIU"), three times a week ("TIW") of interferon alfa-2b and about 600 mg to about 1600 mg/day, orally ("PO") of ribavirin is administered for a first time period of at least about 24 weeks.

7. The method of claim 1 wherein the combination therapy is administered for time period at least about 48 weeks.

8. The method of claim 6 which further comprises administering about 600 to about 1600 mg per day of ribavirin in association with the Vitamin E and Vitamin C for a second time period of at least about 24 weeks after the end of the first time period.

9. The method of claim 7 which further comprises administering about 600 to about 1600 mg/day of ribavirin in association with the Vitamin E and Vitamin C for a third time period of at least about 24 weeks after the end of the first time period.

10. The method of claim 1 wherein the combination therapy comprises about 0.5 to about 1.5 µg/kg, once a week ("QW") of pegylated interferon alfa-2b and about 600 to about 1600 mg/day of ribavirin.

11. The method of claim 1 wherein the combination therapy comprises induction dosing amount of interferon alfa-2b and ribavirin.

12. The method of claim 1 wherein the combination therapy comprises induction therapy dosing of pegylated interferon alfa and ribavirin.

13. A method of treating a patient having chronic HCV infection which comprises administering to said patient a therapeutically effective amount of a combination therapy of pegylated interferon-alfa and ribavirin for a time sufficient to substantially lower HCV-RNA in association with a therapeutically effective amount of Vitamin E and Vitamin C for a time sufficient to ameliorate ribavirin-related hemolysis wherein the therapeutically effective amounts of Vitamin E and of Vitamin C are in the range of about ten to about one hundred times the recommended daily dietary allowance of Vitamin E and of Vitamin C.

14. The method of claim 13 wherein the pegylated interferon alfa is pegylated interferon alfa-2a.

15. The method of claim 13 wherein the pegylated interferon alfa is pegylated interferon alfa-2b.

16. The method of claim 13 wherein the time for administering the combination therapy in association with the therapeutically effective amount of Vitamin E and Vitamin C is a period of at least about 24 weeks.

17. The method of claim 13 wherein the time for administering the combination therapy in association with the therapeutically effective amount of Vitamin E and Vitamin C and is a period of at least about 48 weeks.

18. A method of treating a patient having a chronic HCV infection which comprises administering to said patient for a time period of at least about 24 weeks a therapeutically effective amount of a combination therapy of pegylated interferon alfa and ribavirin sufficient to lower detectable HCV-RNA in association with a therapeutically effective amount of Vitamin E and Vitamin C sufficient to ameliorate ribavirin-related hemolysis wherein the therapeutically effective amounts of Vitamin E and of Vitamin C are in the range of about ten to about one hundred times the recommended daily dietary allowance of Vitamin E and of Vitamin C.

19. The method of claim 18 wherein the patient has a HCV genotype 2 or 3 infection.

20. The method of claim 18 wherein the patient has a HCV genotype 1 infection, and the time period is about 48 weeks.

\* \* \* \* \*

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (ii) MOLECULE TYPE: DNA (oligonucleotide)

(xi) SEQUENCE DESCRIPTION: SEQ ID NO: 1:

GTGGTCTGCG GAACCGGTGA GT      22

(2) INFORMATION FOR SEQ ID NO: 2:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: DNA (oligonucleotide)

(xi) SEQUENCE DESCRIPTION: SEQ ID NO: 2:

TGCACGGTCT ACGAGACCTC      20

-continued (2) INFORMATION FOR SEQ ID NO: 3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 3:

CTGTGAGGAA CTACTGTCTT C                                            21

(2) INFORMATION FOR SEQ ID NO: 4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (oligonucleotide)

(xi) SEQUENCE DESCRIPTION: SEQ ID NO: 4:

CCCTATCAGG CAGTACCACA A                                            21